(12) United States Patent
Hall et al.

(10) Patent No.: US 6,611,324 B1
(45) Date of Patent: Aug. 26, 2003

(54) METHOD FOR TESTING SOLAR CELL ASSEMBLIES BY ULTRAVIOLET IRRADIATION FOR SUSCEPTIBILITY TO ULTRAVIOLET DEGRADATION

(75) Inventors: James T. Hall, Torrance, CA (US); H. Donald Wolpert, Los Angeles, CA (US)

(73) Assignee: TRW Inc., Redondo Beach, CA (US)

( * ) Notice: Subject to any disclaimer, the term of this patent is extended or adjusted under 35 U.S.C. 154(b) by 332 days.

(21) Appl. No.: 09/628,196

(22) Filed: Jul. 28, 2000

(51) Int. Cl.$^7$ .............................................. G01N 21/88
(52) U.S. Cl. .................. 356/237.1; 136/290; 356/239.1
(58) Field of Search ............................. 356/432, 239.1, 356/445, 237.1, 237.2–237.6; 136/290–292; 73/865.6; 250/492.1

(56) References Cited

U.S. PATENT DOCUMENTS

| | | | | |
|---|---|---|---|---|
| 4,874,952 A | * | 10/1989 | Arnaud et al. | 250/455.11 |
| 5,712,709 A | * | 1/1998 | Task et al. | 356/239.1 |
| 6,154,034 A | * | 11/2000 | Lovelady et al. | 324/501 |
| 6,359,212 B1 | * | 3/2002 | Hall et al. | 136/256 |

\* cited by examiner

Primary Examiner—Hoa Q. Pham
Assistant Examiner—Vincent P. Barth

(57) ABSTRACT

A method for determining the susceptibility of solar cell coverglass assemblies to degrade wherein the solar cell assembly contains coated or uncoated coverglass, the method comprises exposing the solar cell coverglass assembly with a pulsing laser having an energy per unit area per pulse which distinguishes by laser damage between coverglass assemblies that have an anomalously high propensity to darken under solar exposure and those that only have a normal, nominal propensity to darken; and, characterizing the propensity of the coverglass assemblies to darken. The process results in an improvement of the long-term power output of solar cells by maintaining optical transparency and reducing temperature increases arising from increased solar absorption in darkened coverglass assemblies.

31 Claims, 1 Drawing Sheet

METHOD FOR TESTING SOLAR CELL ASSEMBLIES BY ULTRAVIOLET IRRADIATION FOR SUSCEPTIBILITY TO ULTRAVIOLET DEGRADATION

CROSS-REFERENCE TO RELATED APPLICATIONS

This application is related to the following two commonly assigned applications:

"Method for Testing Solar Cell Assemblies for Susceptibility to Ultraviolet Degradation," application Ser. No. 09/420,928; and, "Method for Testing Solar Cell Assemblies by Ultraviolet Reflectometry for Susceptibility to Ultraviolet Degradation," application Ser. No. 09/615,385.

BACKGROUND OF THE INVENTION

This invention relates generally to solar cells and solar cell assemblies which are especially useful in space, and more particularly to a method for testing such solar cell assemblies to identify those that have an anomalously high susceptibility to ultraviolet degradation.

Solar panels are conventionally used as a source of electrical power for spacecraft such as satellites. The solar panels typically used for spacecraft include a substrate and a plurality of individual photovoltaic solar cells which are secured to a face surface of the substrate. The individual solar cells are electrically connected together to form a series-parallel solar cell array which, when oriented properly toward the sun, converts solar energy into electrical energy. A coverglass, typically made of a silica material and coated with an optically enhancing layer, covers the individual solar cells and together with the cells forms a solar cell assembly.

The efficiency of a solar cell is directly related to the amount of useful light which is absorbed by the photovoltaic component of solar cell. Only a portion of the light striking the top surface of a solar cell is useful. Another portion of the light striking the cell is non-useful; i.e., the light has wavelengths outside the range that is converted by the cell to electrical power; and yet another portion of light is reflected by the solar cell. To reduce the problem of light reflection, solar cells may employ an antireflective coating on the surface of the coverglass through which light enters. The coating may also serve to reflect non-useful wavelengths of light in order to minimize heating effects.

One of the most important considerations for solar assemblies and panels used on spacecraft is efficiency. If a solar panel degrades in the orbital space environment, it is difficult, if not impossible, to correct or compensate for the resulting loss of electrical power with the result that the useful life of the entire spacecraft is often prematurely ended.

In the deployed configuration, the solar panels are subjected to substantial thermal stresses; the solar cells and the front surfaces of the substrates and coverglasses are subjected to the intense heat of the sun while the back surfaces of the substrates are subjected to the extreme cold of outer space. Furthermore, the coverglasses may be susceptible to degradation (visible darkening) upon exposure to ultraviolet radiation. Some degradation is expected to lead to a normally low, nominal, end-of-life loss in performance. Abnormally high degradation, however, may be caused by defects such as impurities and/or contamination sites present in the coverglass and/or coating. The defects can absorb radiation at a particular ultraviolet wavelength or wavelengths and can result in visible darkening. This darkening of the coverglass or coating results in less useful light being transmitted to the solar cell material, which in turn lowers the efficiency and power generated by the solar cell. The darkening may also significantly contribute to an increase of the temperature of the assembly arising from the increased solar absorption by the darkened coverglass.

Conventional quality control methods for inspecting solar cell coverglasses examine properties such as trace element levels in the glass substrate and UV reflectance coatings, multilayer coating thickness, and optical quality. These measurements do not necessarily correlate with the propensity of a coverglass or coating to darken on-orbit. Further, these methods are susceptible to passing solar cell assemblies that initially meet quality specifications, but later visibly darken upon ultraviolet-induced degradation. It thus is desirable to provide a test method that identifies the susceptibility of the solar cell assemblies to darkening and degradation before putting them in orbit.

SUMMARY OF THE INVENTION

The aforementioned need in the prior art is met by the present invention which provides a method for determining the susceptibility of a solar cell coverglass assembly to degrade wherein the solar cell coverglass assembly is one of coated and uncoated coverglass. The method comprises the steps of (1) exposing the solar cell coverglass assembly to a pulsing laser source having an energy per unit area per pulse which is preselected to cause damage to a coverglass assembly having an anomalously high propensity to darken and leave undamaged a solar cell coverglass assembly having only a nominal, lower propensity to darken; (2) identifying damage caused by the laser; and, (3) characterizing the propensity of the coverglass to darkening as a function of damage.

BRIEF DESCRIPTION OF THE DRAWING

Reference is now made to the Description of the Preferred Embodiment, illustrated in the accompanying drawings, in which.

DESCRIPTION OF THE PREFERRED EMBODIMENT

Figure 1:
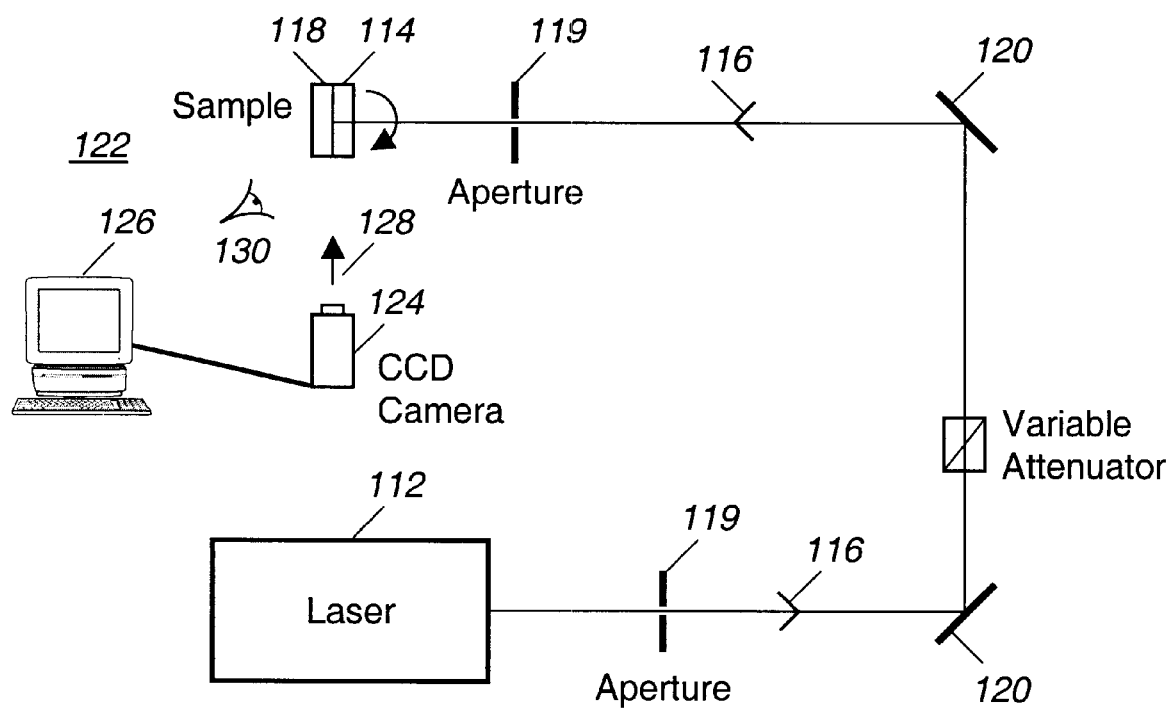
FIG. 1 is a schematic illustration of an apparatus utilized to conduct the testing of the solar cell coverglass for darkening in accordance with the present invention.

The purpose of the present invention is to relatively quickly determine if a solar cell will darken when placed on a spacecraft and positioned in a space environment. The present invention illuminates the solar cell and coverglass with a laser source which is set to a preselected energy level. It has been determined that a solar cell coverglass coating that is anomalously more susceptible to darkening has a lower laser damage threshold than a solar cell coverglass coating that is only nominally less susceptible to darkening. As such, the coverglass can be tested for susceptibility to darkening by exposing the coverglass to a pulsed laser source having an energy per unit area per pulse which is sufficient to damage uncoated or coated coverglass having a high propensity to darken, but of an insufficient energy per unit area per pulse to damage coverglass or coating that is free of a high propensity to darken. After exposure, the coverglass surface is inspected for signs of laser damage where laser damage appears on the coverglass as a new small pit or a new light scattering site. The invention is particularly applicable for testing solar cell coverglass assemblies which are mounted to or are covering an underlying solar cell.

Referring to FIG. 1, the method of the present invention is preferably performed using testing apparatus 100 which includes a laser source 112 which is configured to expose the solar cell coverglass 114 to laser light, depicted by the line marked 116. The laser source 112 is preferably a pulsed laser source and is preferably positioned to be adjacent to the coverglass 114 but may also be located remote from the glass 114 with reflecting mirrors 120 being used to route the laser light 116 to the coverglass 114.

The laser source 112 is configured so that the energy per unit area per pulse 116 is greater than that which would cause damage to solar cell coverglass having an anomalously high propensity to darken but below a level which would cause damage to solar cell coverglass having only a nominal, lower propensity to darken. As such, a single pulse can cause visible damage on a coverglass 114 that has a propensity to darken.

The energy per unit area per pulse at which the laser source 112 is set for the darkening test is determined by a preliminary threshold level test. To determine the threshold level, one or more coverglass samples are illuminated with a relatively low energy level (e.g., 1 mJ/cm² per pulse). The energy level is subsequently increased until damage to the coverglass 114 is detected. The laser 112 is then set to a level which is in between the non-damaging level and the damaging level. All coverglass 114 is then tested at this laser level. At this laser level, coverglass 114 having a propensity to darkening will experience damage whereas coverglass not having a propensity to darken will not exhibit damage.

As an example, Table 1 shows the test data taken from five coverglass samples. Each sample was illuminated with laser light at a low energy per unit area per pulse of 1 mJ/cm² per pulse. The energy per unit area per pulse of the laser was slowly increased until damage was noticed on the coverglass. The energy per unit area per pulse at which the damage occurred is referred to as the threshold fluence in Table 1. As shown in Table 1, for test sample #1, the damage occurred at 22 mJ/cm² per pulse whereas, for sample #2, the damage did not occur until 35 mJ/cm² per pulse was achieved. As evidenced by the data shown in Table 1, each sample experienced damage at a different energy per unit area per pulse. Each sample was then tested by other means known to one practiced in the art for a propensity to darken. Samples 1, 3 and 4 exhibited an anomalously high propensity to darkening after about one year of equivalent solar vacuum ultraviolet exposure in geosynchronous orbit. Samples 2 and 5 did not. In particular, samples 1, 3, and 4 suffered from darkening that resulted in over 5% to 6% loss in efficiency to a silicon solar cell. In contrast, samples 2 and 5 suffered only less than 1% to 2% loss, an expected nominal value for one year of equivalent solar exposure. As expected, the samples which subsequently darkened to an anomalously high level had a lower laser damage threshold level than those that did not subsequently darken anomalously. In particular, for this sample set, an energy per unit area per pulse between 15.7 and about 27.7 mJ/cm² per pulse damaged coverglass having a propensity to darken but did not damage coverglass which was free of a propensity to darken.

TABLE 1

Laser Damage Thresholds for Coated Surfaces
(wavelength = 193 nm, pulsewidth = 10 ns)

| Sample | Damage Threshold Fluence (mJ/Cm²) | Anomalously High Propensity to Darken |
|---|---|---|
| 1 | 22 | Yes |
| 2 | 35 | No |
| 3 | 15.7 | Yes |
| 4 | 27.7 | Yes |
| 5 | 31.5 | No |

It was thus determined from these types of experiments that an energy per unit area per pulse of about 30 mJ/cm² per pulse will cause damage in coverglass having an anomalously high propensity to darken but will not damage coverglass which is free of a high propensity to darken. The value of 30 mJ/cm² per pulse is just one useful discriminating value for this particular example of coverglass with a particular coating tested by a particular laser. Depending on the type of laser (exact ultraviolet wavelength, exact pulse width, shape of pulse, etc.) and depending on coverglass (with or without coating, propensity to darken, etc.), other values may be useful.

Referring back to FIG. 1, the laser source is preferably configured to provide the laser light 116 at a wavelength of approximately 193 nm because solar cell coverglass 114 is typically made of a material which protects the underlying solar cell from radiation at 193 nm. Thus, a 193 nm source will not damage the underlying solar cell, and the solar cell coverglass 114 can be tested for a propensity to darken while covering the solar cell 118. A pulsing argon fluoride (ArF₂) laser that produces a pulsewidth of about 5 ns to 30 ns is adequate for performing this test.

The testing of the coverglass 114 occurs as follows. The energy per unit area per pulse of the laser source 112 is set to the preselected value and the coverglass 114 is exposed to the laser light. After exposure to the laser light 116, the solar cell coverglass 114 is examined for damage and is characterized by other means known to one practiced in the art as either having an anomalously high propensity to darken or not having an anomalously high propensity to darken. To do so, the operator of the testing apparatus 100, or an inspector, examines the solar cell coverglass 114 with a naked eye 130 or with magnification assisting the naked eye 130. The operator then determines whether or not the glass surface 114 was damaged by the laser. Coverglass or coating which is damaged by the laser at the present level is characterized as having an anomalously high propensity to darken whereas coverglass which is not damaged by the laser is characterized as having only a nominally low propensity to darken.

Damage to the coverglass and/or coating 114 can also be detected with the aid of a measurement device 122. The measurement device 122 can be any mechanical, optical or electrical device known to one skilled in the art to measure damage to coverglass 114 but preferably is a CCD camera 124 coupled to a display unit 126. The CCD camera 124 is configured to detect a pit or visibly scattered light 128 from the coverglass 114. A hazy appearance in the display of the detected light results from scattered light, which in turn reveals a damage site in the coverglass. Alternatively, pre and post laser exposure scattering measurements can be compared for an indication of laser damage. An increased change in the scattering measurement indicates laser-induced damage and therefore, a higher susceptibility to darkening.

What has been described is an improved process for determining whether or not solar cell coverglasses and/or their coatings either exhibit or have a propensity for exhibiting darkening, thereby resulting in an improvement of the long-term power output of solar cells by maintaining optical transparency and reducing temperature increases arising from increased solar absorption in darkened coverglasses.

It will be appreciated by persons skilled in the art that the present invention is not limited to what has been shown and described hereinabove. The scope of the invention is limited solely by the claims which follow.

We claim as our invention:

1. A method for determining the susceptibility of a solar cell coverglass assembly to darken, wherein the solar cell coverglass assembly is a coated coverglass, the method comprising:
    exposing the solar cell coverglass assembly with a pulsing laser source having an energy per unit area per pulse which damages a solar cell coverglass assembly having an anomalously high propensity to darken and leaves undamaged a solar cell coverglass assembly which is free of such a propensity to darken;
    inspecting the solar cell coverglass assembly after exposure; and
    characterizing the coverglass assembly for susceptibility to darkening.

2. The method of claim 1, wherein characterizing the coverglass assembly comprises visually examining the coverglass assembly for visible evidence of laser damage which will result in scattering of light indicative of a susceptibility to darken.

3. The method of claim 1, wherein inspecting comprises measuring scattering of visible light from the coverglass assembly before and after exposure of the solar cell coverglass assembly; and,
    wherein characterizing comprises comparing the before and after level of scattering, a change in the scattering level indicating an anomalously high susceptibility to darkening.

4. The method of claim 1, wherein exposing the solar cell coverglass assembly comprises exposing the solar cell coverglass assembly to a pulsing laser having an energy per unit area per pulse which is preselected to damage only coverglass assemblies having an anomalously high propensity to darken due to a low laser damage threshold.

5. The method of claim 4, wherein exposing the solar cell coverglass assembly comprises exposing the solar cell coverglass to a pulsing laser that emits 193 nm wavelength light with a pulse width between about 5 and 30 ns and having an energy level, the actual value being dependent on the characteristics of the solar cell assembly including the coating material if present.

6. The method of claim 4, further comprising determining a laser damage threshold level for coverglass assemblies having a propensity to darken, whereby the laser damage threshold level is dependant on at least one characteristic of the laser comprising wavelength, pulsewidth and temporal shape of pulse as well as on type of coverglass assembly under test.

7. The method of claim 1, wherein inspecting comprises detecting visibly scattered light from the coverglass assembly and generating therefrom a display of the scattered light.

8. A method for testing a solar cell coverglass assembly covering a solar cell for a susceptibility to darkening, comprising:
    exposing the solar cell and coverglass assembly to a laser source having an energy per unit area per pulse which is greater than that which would damage a coverglass assembly having an anomalously high propensity to darken and leave undamaged a coverglass assembly which is free of such a propensity to darken; and,
    characterizing the coverglass assembly for susceptibility to darkening.

9. The method of claim 8, further comprising conducting a pre-exposure scattering measurement of the coverglass assembly covering the solar cell; and
    conducting a post-exposure scattering measurement of the coverglass assembly; and wherein characterizing comprises:
        characterizing the coverglass assembly for susceptibility to darken by comparing the pre and post-exposure scattering measurements, an increased change in the scattering measurement indicating laser-induced damage and therefore a higher susceptibility to darkening.

10. The method of claim 8, wherein characterizing comprises inspecting the solar cell coverglass assembly for visible indications of damage indicating a higher propensity to darken.

11. The method of claim 8, wherein exposing the solar cell coverglass assembly comprises exposing the solar cell coverglass assembly with a pulsing laser having an energy per unit area per pulse which is preselected to damage only a coverglass assembly having an anomalously high propensity to darken due to a low laser damage threshold.

12. The method of claim 8, further comprising determining a laser damage threshold level for a coverglass assembly having a propensity to darken, whereby the laser damage threshold level is dependant on at least one characteristic of the laser comprising wavelength, pulsewidth and temporal shape of pulse as well as a type of the coverglass assembly under test.

13. The method of claim 8, further comprising detecting visibly scattered light from the coverglass assembly and generating therefrom a display of the scattered light.

14. A method for determining the susceptibility of a solar cell coverglass assembly to darken, wherein the solar cell coverglass assembly is an uncoated coverglass, the method comprising:
    exposing the solar cell coverglass assembly with a pulsing laser source having an energy per unit area per pulse which damages a solar cell coverglass assembly having an anomalously high propensity to darken and leave undamaged a solar cell coverglass assembly which is free of such a propensity to darken;
    inspecting the solar cell coverglass assembly after exposure; and
    characterizing the coverglass assembly for susceptibility to darkening.

15. A method for determining the susceptibility of a solar cell coverglass assembly to darken, wherein the solar cell coverglass assembly is a combination of coated and uncoated coverglasses, the method comprising:
    exposing the solar cell coverglass assembly with a pulsing laser source having an energy per unit area per pulse which damages a solar cell coverglass assembly having an anomalously high propensity to darken and leave undamaged a solar cell coverglass assembly which is free of such a propensity to darken;
    inspecting the solar cell coverglass assembly after exposure; and
    characterizing the coverglass assembly for susceptibility to darkening.

16. The method of claim 14, wherein characterizing the coverglass assembly comprises visually examining the coverglass assembly for visible evidence of laser damage which will result in scattering of light indicative of a susceptibility to darken.

17. The method of claim 14, wherein inspecting comprises measuring scattering of visible light from the coverglass assembly before and after exposure of the solar cell coverglass assembly; and, wherein characterizing comprises comparing the before and after level of scattering, a change in the scattering level indicating an anomalously high susceptibility to darkening.

18. The method of claim 14, wherein exposing the solar cell coverglass assembly comprises exposing the solar cell coverglass assembly to a pulsing laser having an energy per unit area per pulse which is preselected to damage only coverglass assemblies having an anomalously high propensity to darken due to a low laser damage threshold.

19. The method of claim 18, wherein exposing the solar cell coverglass assembly comprises exposing the solar cell coverglass to a pulsing laser that emits 193 nm wavelength light with a pulse width between about 5 and 30 ns and having an energy level, the actual value of the pulsewidth and energy level being dependent on the characteristics of the solar cell coverglass assembly including the coating material if present.

20. The method of claim 18, further comprising determining a laser damage threshold level for coverglass assemblies having a propensity to darken, whereby the laser damage threshold level is dependant on at least one characteristic of the laser comprising wavelength, pulsewidth and temporal shape of pulse as well as on type of coverglass assembly under test.

21. The method of claim 14, wherein inspecting comprises detecting visibly scattered light from the coverglass assembly and generating therefrom a display of the scattered light.

22. The method of claim 14, further comprising conducting a pre-exposure scattering measurement of the coverglass assembly covering the solar cell; and conducting a post-exposure scattering measurement of the coverglass assembly; and wherein characterizing comprises:
characterizing the coverglass assembly for susceptibility to darken by comparing the pre and post-exposure scattering measurements, an increased change in the scattering measurement indicating laser-induced damage and therefore a higher susceptibility to darkening.

23. The method of claim 14, wherein characterizing comprises inspecting the solar cell coverglass assembly for visible indications of damage indicating a higher propensity to darken.

24. The method of claim 15, wherein characterizing the coverglass assembly comprises visually examining the coverglass assembly for visible evidence of laser damage which will result in scattering of light indicative of a susceptibility to darken.

25. The method of claim 15, wherein inspecting comprises measuring scattering of visible light from the coverglass assembly before and after exposure of the solar cell coverglass assembly; and, wherein characterizing comprises comparing the before and after level of scattering, a change in the scattering level indicating an anomalously high susceptibility to darkening.

26. The method of claim 15, wherein exposing the solar cell coverglass assembly comprises exposing the solar cell coverglass assembly to a pulsing laser having an energy per unit area per pulse which is preselected to damage only coverglass assemblies having an anomalously high propensity to darken due to a low laser damage threshold.

27. The method of claim 26, wherein exposing the solar cell coverglass assembly comprises exposing the solar cell coverglass to a pulsing laser that emits 193 nm wavelength light with a pulsewidth between about 5 and 30 ns and having an energy level, the actual value of the pulsewidth and energy level being dependent on the characteristics of the solar cell coverglass assembly including the coating material if present.

28. The method of claim 26, further comprising determining a laser damage threshold level for coverglass assemblies having a propensity to darken, whereby the laser damage threshold level is dependant on at least one characteristic of the laser comprising wavelength, pulsewidth and temporal shape of pulse as well as on type of coverglass assembly under test.

29. The method of claim 15, wherein inspecting comprises detecting visibly scattered light from the coverglass assembly and generating therefrom a display of the scattered light.

30. The method of claim 15, further comprising conducting a pre-exposure scattering measurement of the coverglass assembly covering the solar cell; and conducting a post-exposure scattering measurement of the coverglass assembly; and wherein characterizing comprises:
characterizing the coverglass assembly for susceptibility to darken by comparing the pre and post-exposure scattering measurements, an increased change in the scattering measurement indicating laser-induced damage and therefore a higher susceptibility to darkening.

31. The method of claim 15, wherein characterizing comprises inspecting the solar cell coverglass assembly for visible indications of damage indicating a higher propensity to darken.

* * * * *